United States Patent

Claussner et al.

Patent Number: 5,434,176
Date of Patent: Jul. 18, 1995

[54] PHENYLIMIDAZOLIDINES

[75] Inventors: André Claussner, Villemomble; Francois Goubet, Paris; Jean-Georges Teutsch, Pantin, all of France

[73] Assignee: Roussel UCLAF, France

[21] Appl. No.: 68,736

[22] Filed: May 28, 1993

[30] Foreign Application Priority Data

Jul. 8, 1992 [FR] France .................. 92 08432

[51] Int. Cl.$^6$ .......................... A61K 31/415
[52] U.S. Cl. .................... 514/391; 548/301.4
[58] Field of Search .............. 548/301.4; 514/391

[56] References Cited

U.S. PATENT DOCUMENTS

| | | | |
|---|---|---|---|
| 379,038 | 1/1975 | Magnani | 514/391 |
| 4,473,393 | 9/1984 | Nagpal | 71/92 |
| 4,753,957 | 6/1988 | Chan | 514/391 |
| 4,944,791 | 7/1990 | Schröder et al. | 548/278 |
| 5,084,472 | 1/1992 | Moguilewsky et al. | 514/389 |

FOREIGN PATENT DOCUMENTS

| | | |
|---|---|---|
| 0001813 | 5/1979 | European Pat. Off. |
| 0091596 | 10/1983 | European Pat. Off. |
| 0436426 | 7/1991 | European Pat. Off. |
| 0494819 | 7/1992 | European Pat. Off. |
| 2075751 | 9/1971 | France |
| 2329276 | 10/1975 | France |

OTHER PUBLICATIONS

Chemical Abstracts vol. 114, No. 119, Abst. No. 185374 (1991).
Kruger et al., Arch. Pharm 311, pp. 39–47 (1978).
CA. 81, No. 7, Aug. 19, 1984.

Primary Examiner—Joseph Paul Brust
Attorney, Agent, or Firm—Bierman and Muserlian

[57] ABSTRACT

A compound selected from the group consisting of compounds of the formula

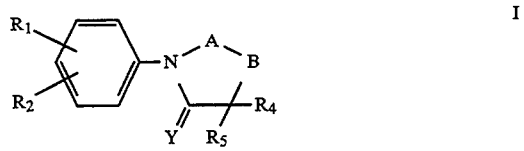

I wherein $R_1$ and $R_2$ are individually selected from the group consisting of —CN, —NO$_2$, halogen, —CF$_3$, free carboxy, salified carboxy, and carboxy esterified with lower alkyl; -A-B- is selected from the group consisting of

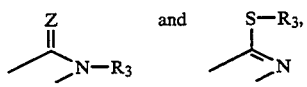

and X, $R_3$, $R_4$ and $R_5$ are defined as in the specification and their non-toxic, pharmaceutically acceptable acid addition salts having anti-androgenic activity.

8 Claims, No Drawings

PHENYLIMIDAZOLIDINES

STATE OF THE ART

Japanese application No. J 48087030 describes 3-phenyl-2-thiohydantoins useful for inhibiting the germination of certain plants. U.S. Pat. No. 4,907,518 describes imidazolidines different from Formula I having anti-androgenic activity. Other pertinent art includes U.S. Pat. Nos. 3,823,240; 4,873,256; 4,407,814; 4,482,739 and 4,234,736.

OBJECTS OF THE INVENTION

It is an object of the invention to provide novel compounds of Formula I and their non-toxic, pharmaceutically acceptable acid addition salts, novel intermediates, and a novel process for the preparation of the compounds.

It is another object of the invention to provide novel anti-androgenic compositions and a novel method of inducing anti-androgenic activity in warm-blooded animals.

These and other objects and advantages of the invention will become obvious from the following detailed description.

THE INVENTION

The novel phenylimidazolidines of the invention have the Formula

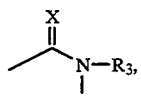
I wherein $R_1$ and $R_2$ are individually selected from the group consisting of —CN, —NO$_2$, halogen, —CF$_3$, free carboxy, salified carboxy and carboxy esterified with lower alkyl, -A-B- is selected from the group consisting of

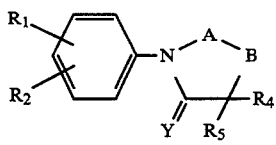

X, is —O— or —S—, $R_3$ is selected from the group consisting of hydrogen, alkyl, alkenyl and alkynyl all of up to 12 carbon atoms, aryl and aralkyl of up to 12 carbon atoms, all optionally substituted with at least one member of the group consisting of —OH, halogen, —SH, —CN, acyl of up to 7 carbon atoms, acyloxy of up to 7 carbon atoms, —S— aryl of up to 12 carbon atoms optionally substituted with a member of the group consisting of —CF$_3$, alkyl, alkoxy, alkenyl, alkenyloxy, alkynyl and alkynyloxy, with the sulfur being optionally oxidized to sulfone or sulfoxide, free, esterified, amidified or salified carboxy, —NH$_2$, mono and dialkylamino and heterocyclic of 3 to 6 ring members and containing at least one heteroatom selected from the group consisting of oxygen, sulfur, and nitrogen, the alkyl, alkenyl, and alkynyl being optionally interrupted with at least one member of the group consisting of oxygen, nitrogen, and sulfur optionally oxidized to sulfoxide or sulfone, Y is —O—, —S— or =NH, $R_4$ and $R_5$ are individually selected from the group consisting of hydrogen and alkyl of up to 12 carbon atoms optionally substituted with at least one halogen or, taken together with the carbon atom to which they are attached, form cycloalkyl of 3 to 7 carbon atoms except the compounds wherein $R_4$ and $R_5$ are both methyl or one is hydroxymethyl, Y is —O— or =NH—, -A-B- is

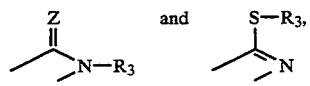

X is is oxygen, $R_3$ is hydrogen, $R_1$ is 4-NO$_2$ and $R_2$ is 3—CF$_3$; and their non-toxic, pharmaceutically acceptable acid addition salts.

The following examples of Alkyl of up to 12 carbon atoms includes methyl, ethyl, propyl, isopropyl, butyl, isobutyl, sec.-butyl, tert.-butyl, pentyl, isopentyl, sec.-pentyl, tert.-pentyl, neopentyl, hexyl, isohexyl, sec.-hexyl, tert.-hexyl, heptyl, octyl, decyl, undecyl, and dodecyl, whether branched or linear. Preferred are alkyl of 1 to 4 carbon atoms, especially methyl, ethyl, propyl, isopropyl.

Examples of alkenyl of up to 12 carbon atoms are vinyl, allyl, 1-propenyl, butenyl, pentenyl, hexenyl, preferably alkenyl of 2 to 4 carbon atoms, and especially butenyl or allyl. Examples of alkynyl of up to 12 carbon atoms are ethynyl, propargyl, butynyl, pentynyl and hexynyl, preferably 2 to 4 carbon atoms such as propargyl. Examples of cycloalkyl are cyclopropyl, cyclobutyl, cyclopentyl, cyclohexyl, cycloheptyl and cyclooctyl.

Examples of aryl are carbocyclic aryl such as phenyl and naphthyl, heterocyclic aryl of 5 to 6 ring members containing at least one heteroatom selected from the group consisting of oxygen, sulfur, and nitrogen. Examples of 5 membered ring heteroaryls are furyl, thienyl, pyrrolyl, thiazolyl, oxazolyl, imidazolyl, thiadiazolyl, pyrazolyl, and isoxazolyl. Examples of 6 membered ring heteroaryl are pyridyl, pyrimidinyl, pyridazinyl, and pyrazinyl. Examples of condensed aryls are indolyl, benzofuranyl, benzothienyl and quinoleinyl. The preferred aryl is phenyl.

Examples of aralkyl include the alkyls recited above substituted with the aryls cited above. The preferred aralkyls are phenethyl and benzyl. Examples of halogen are fluorine, chlorine, bromine, and iodine, but preferred are fluorine, chlorine, and bromine. Examples of alkyl substituted with at least one halogen are fluoromethyl, chloromethyl, bromomethyl, iodomethyl, difluoromethyl, dichloromethyl, dibromomethyl, and trifluoromethyl.

Examples of substituents for aryl and aralkyl are phenyl substituted by fluorine, —OCH$_3$, or —CF$_3$ in the p-position. Examples of acyl are preferably those of up to 7 carbon atoms, such as acetyl, propionyl, butyryl, and benzoyl, as well as valeryl, hexanoyl, acryloyl, crotonoyl, carbamoyl, and formyl. The acyloxy may be derived from the same acids, especially acetyloxy and propionyloxy.

The esterified carboxy may be alkoxycarbonyl such as methoxycarbonyl, ethoxycarbonyl, propoxycarbonyl, butoxycarbonyl, tert.-butoxycarbonyl, cyclobutyloxy carbonyl, cyclopentyloxy carbonyl and cyclohexyloxy carbonyl.

Examples of easily cleavable esters include methoxymethyl, ethoxymethyl, acyloxyalkyl such as pivaloyloxymethyl, pivaloyloxyethyl, acetoxymethyl, and acetoxyethyl; alkoxycarbonyloxyalkyl such as methoxycarbonyloxymethyl, methoxycarbonyloxyethyl, isopropoxycarbonyloxymethyl, and isopropoxycarbonyloxyethyl. Other esters are described in European Patent No. 0,034.536.

The amidified carboxy are of the type

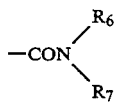

wherein $R_6$ and $R_7$ are individually selected from the group consisting of hydrogen and alkyl of 1 to 4 carbon atoms such as methyl, ethyl, propyl, isopropyl, butyl, isobutyl, sec.-butyl and tert.butyl.

Examples of mono and dialkylamino are methylamino, ethylamino, dimethylamino, diethylamino, and methylethylamino. The heterocyclic of 5 to 6 ring members optionally containing another heteroatom of

may be pyrrolyl, imidazolyl, pyridyl, pyrazinyl, pyrimidyl, indolyl, piperidino, morpholino, and piperazinyl, preferably piperidino or morpholino.

Examples of salts of salified carboxy are sodium, potassium, lithium, calcium, magnesium, ammonium, and organic bases such as methylamine, propylamine, trimethylamine, diethylamine, and triethylamine. Sodium salts are preferred.

The alkylamino and dialkylamino are preferably alkyl of 1 to 4 carbon atoms such as methylamino, ethylamino, propylamino, isopropylamino, butylamino, dimethylamino, diethylamino, and ethylmethylamino. Examples of the heterocyclics containing at least one heteroatom are saturated monocyclics such as oxirannyl, oxolannyl, dioxolannyl, imidazolidinyl, pyrazolidinyl, piperidyl, piperazinyl, and morpholinyl.

The alkyl, alkenyl, and alkynyl are optionally interrupted by one or more sulfur, oxygen, or nitrogen heteroatoms. Examples are alkoxyalkyl such as methoxymethyl, methoxyethyl, methoxypropyl, and methoxybutyl, as well as alkoxy alkoxyalkyl such as methoxyethoxymethyl.

When the products of Formula I contain a salifiable amino group, the acid addition salts of non-toxic, pharmaceutically acceptable acids may be formed. Examples of said acids are inorganic acids such as nitric acid, hydrochloric acid, sulfuric acid, and phosphoric acid, as well as organic acids such as formic acid, acetic acid, propionic acid, benzoic acid, and methane sulfonic acid.

Among the preferred compounds of Formula I are those wherein Y is oxygen, -A-B- is

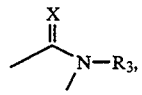

and X and $R_3$ are defined as above; those wherein -A-B- is

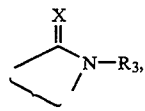

X has the above definition, and $R_3$ is hydrogen or alkyl of 1 to 6 carbon atoms optionally interrupted by at least one of —O—, —S—, and optionally substituted by —OH, —OH esterified with an acyl of an organic carboxylic acid of 1 to 7 carbon atoms, or free, esterified, or salified carboxy, are also worthy of special mention.

Among the preferred compounds of Formula I are those wherein $R_3$ is hydrogen or alkyl of 1 to 6, preferably 1 to 4, carbon atoms optionally substituted with —OH; those wherein $R_2$ is 3—$CF_3$ and $R_1$ is 4-CN; those wherein $R_4$ and $R_5$ are individually hydrogen, ethyl, or —$CF_3$; and those wherein $R_4$ and $R_5$ together with the carbon atoms form cyclobutyl or cyclopentyl.

Specific preferred compounds of Formula I are 4-(3-methyl-5-oxo-2-thioxo-1-imidazolidinyl)-2-(trifluoromethyl)-benzonitrile, 4-[1-methyl-4-oxo-2-thioxo-1,3-diazaspiro (4,4)-nonan-3-yl]-2(tri-fluoromethyl)-benzonitrile, and 4-(4,4-diethyl-3-methyl-5-oxo-2-thioxo-1-imidazolidinyl)-2-(trifluoromethyl)-benzonitrile.

The inventive process for the preparation of a compound of Formula I comprises reacting the compound of the Formula

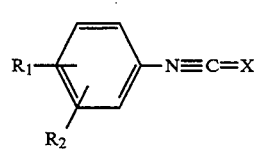

wherein $R_1$, $R_2$, and X have the above definitions, with a compound of the Formula

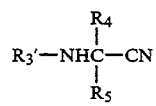

in the presence of a tertiary base, wherein $R'_3$ has the definition of $R_3$ with the active functions optionally protected, $R_4$ and $R_5$ have the above definitions with the proviso that $R_4$ and $R_5$ are not both methyl and, if $R_1$ is 4-$NO_2$, $R_2$ is 3—$CF_3$, X is —O—, and $R'_3$ is hydrogen; and if one of $R_1$ or $R_5$ is —$CH_3$, the other is —$CH_2OH$ to obtain a compound of the formula

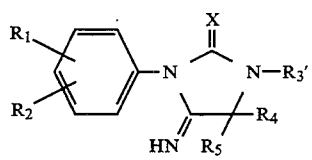

wherein $R_1$, $R_2$, X, $R'_3$, $R_4$ and $R_5$ have the above definitions and optionally subjecting the latter to at least one of the following reactions in any order:

a) elimination of the optional protective groups of $R'_3$;

b) hydrolysis of C=NH to a ketone function and if appropriate of >C=S to >C=O;

c) transformation of >C=O to >C=S, and d) reaction of the products of Formula IV wherein R'₃ is hydrogen after hydrolysis of >C=NH to a ketone, with a compound of the formula R"₃-Hal, wherein Hal is halogen and R"₃ is R'₃ except hydrogen to obtain a compound of Formula I wherein -A-B- is

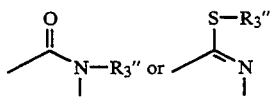

in which R"₃ has the above meaning; then if desired, the reaction of these products with an elimination agent for the optional protective groups that can be carried by R"₃ or, if appropriate, the reaction with an esterification, amidification, or salification agent, or reacting a compound of the Formula

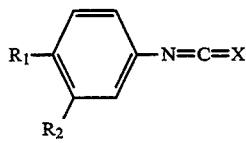

II wherein R₁, R₂ and X have the above definitions, in the presence of a tertiary base, with a compound of the formula

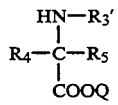

III' wherein R'₃, R₄ and R₅ have the above definitions and Q is an alkali metal such as sodium or alkyl of 1 to 6 carbon atoms, to obtain a compound of the formula

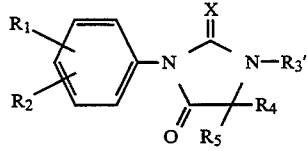

IVa wherein R₁, R₂, X, R'₃, R₄ and R₅ have the above definitions and optionally subjecting compound IVa to any one or more of the following reactions in any order:

a) elimination of the optional protective groups that can be carried by R'₃;

b) conversion of the >C=O group or groups into >C=S or, if appropriate conversion of >C=S into >C=O;

c) reaction of the products of Formula IVa, in which R'₃ is hydrogen, with a reagent of formula Hal-R"₃, wherein R"₃ is the same as R'₃ with the exception of hydrogen and Hal is halogen, to obtain the products of Formula I in which -A-B-is

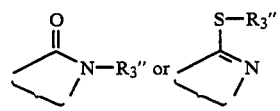

and optionally reaction of the latter to eliminate the protective group of R"₃, or reaction of the same with an esterification, salification or amidification agent, or reaction of a compound of the formula R"₃-Hal as defined above with a compound of the formula

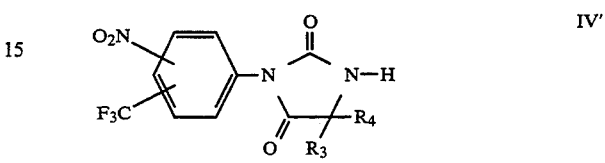

IV' to obtain a compound of the formula

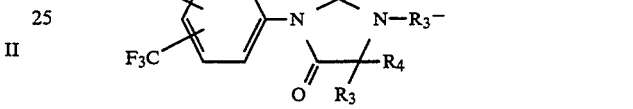

IV"

and optionally subjecting the latter to at least one of the following reactions:

a) elimination of optional protective groups of R"₃ and then reaction with an esterification, salification or amidification agent; and b) transformation of >C=O to >C=S.

The reaction of the products of Formula II with the products; of Formula III is preferably effected in an organic solvent such as tetrahydrofuran, dichloroethane, ethyl ether, or isopropyl ether in the presence of a tertiary base such as triethylamine, pyridine, methylethyl pyridine.

The optional reactive functional groups of R₃ which are optionally protected in compounds of Formula III, IVa, or IV" are —OH or amino which are protected by the usual protective groups. Examples of such protective groups for —NH2 are tert.-butyl, tert.-amyl, trichloroacetyl, chloroacetyl, benzhydryl, trityl, formyl and benzyloxycarbonyl. Examples of hydroxy protective groups are formyl, chloroacetyl, tetrahydropyranyl, trimethylsilyl, and tert.butyldimethylsilyl.

The above list of protective groups is not intended to be exhaustive and any protective group known, for example, in peptide chemistry may be used. Other known protective groups are described in French Patent 2,499,995 which is incorporated herein by reference. The optional reactions to eliminate groups are indicated in the said patent and the preferred method of elimination is acid hydrolysis with hydrochloric acid, benzene sulfonic acid, p-toluene sulfonic acid, formic acid, or trifluoroacetic acid, preferably hydrochloric acid.

The optional hydrolysis of >C=NH to >C=O is preferably effected by reaction with refluxing aqueous hydrochloric acid. When the hydrolysis of >C=NH to >C=O is effected with a molecule also containing >C=S, the latter may be transformed into a >C=O group. The free hydroxy optionally contained in R₃ may also be transformed into —SH.

The transformation of >C=O into >C=S is effected with a Lawesson reagent of the formula

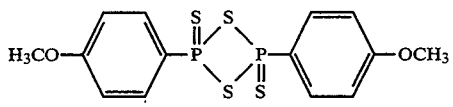

which is commercial product sold, for example, by Fluka and is described in Bull. Soc. Chim. Belg., Vol. 87 No. 3 (1987), p. 229. When two >C=O groups are changed to >C=S, the reaction is effected with an excess of the Lawesson reagent. The same is also used when the molecule contains both >C=O to >C=S.

On the other hand, when part of the molecule contains two >C=O's, and it is desired to obtain a product with only one >C=S, a deficiency of the Lawesson reagent is used to obtain a mixture of 3 products, each of two products with a >C=O and >C=S and one containing two >C=S's. These products can be separated by known methods such as chromatography.

The reaction of the compounds of Formulas IV, IVA, or IV' with a compound of the formula R"$_3$-Hal is effected in the presence of a strong base such as sodium hydride or potassium hydride in a phase transfer reaction in the presence of quaternary ammonium salts such as tert.-butyl ammonium The protective groups of R"$_3$ may be those discussed above for R$_3$. The reaction to eliminate the protective groups are as discussed above. For example, a tert-butyl dimethylsilyl group may be removed by hydrochloric acid as described in the examples herein.

The optional esterification of the compounds of Formula I wherein R"$_3$ is free —OH is effected under classical conditions using, for example, an acid or a functional derivative thereof such as its anhydride, e.g. acetic acid anhydride, in the presence of a base such as pyridine. The optional esterification or salification of the compounds of Formula I wherein R"$_3$ is —COOH may be effected by known methods.

The optional amidification of the compounds of Formula I wherein R"$_3$ is —COOH is also effected under classical conditions with primary or secondary amines with functional derivatives of —COOH, such as a symmetrical or mixed anhydride thereof.

The process of the invention to prepare compounds of the Formula

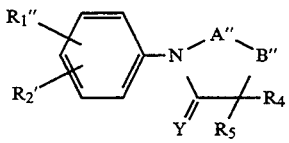           I"

wherein R"$_1$, R"$_2$, and -A"-B"- have the definitions of R$_1$ and R$_2$, and -A-B-, except that, when -A"-B"- is

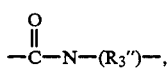

and R"$_3$ is hydrogen or alkyl of 1 to 7 carbon atoms and Y is oxygen R"$_1$ is —CN, comprises reacting a compound of the Formula

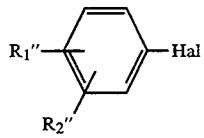           V wherein R"$_1$ and R"$_2$ have the above definitions and Hal is halogen with a compound of the formula

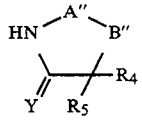           VI wherein -A"-B"-, R$_4$, and Y have the above definitions, in the presence of a catalyst and optionally a solvent. In the compounds of formula V, the halogen is preferably chlorine but may be iodine or bromine.

The role of the catalyst is obviously to trap the hydrogen halide as it forms and to facilitate the condensation reaction of the compounds of Formulas V and VI to form the desired product. The catalyst is preferably a metal in its native form, its oxide, its salt, or it may be a base. When the catalyst is metal, it is preferably copper or nickel and the metallic salts are preferably the chloride or acetate. When the catalyst is a base, it is preferably sodium hydroxide or potassium hydroxide and dimethylsulfoxide may be added to the reaction medium.

The catalyst of the process may be selected from cuprous oxide, cupric oxide, metallic copper, or a base such as sodium hydroxide or potassium hydroxide, preferably cuprous oxide in powdered form. The solvent used preferably is a high boiling point ether such as phenyl oxide, diglyme, triglyme, or dimethylsulfoxide; also useful are high boiling point oils such as paraffin or petroleum jelly. Preferably, the process is effected in an ether solvent such as phenyl oxide, diglyme, triglyme or dimethylsulfoxide, most preferably in phenyl oxide or triglyme.

The process may be effected at atmospheric pressure or under pressure at temperatures above 100° C., preferably above 150° C., for more than two hours. The reaction is preferably effected with cuprous oxide in triglyme at temperatures of 200° C. or higher for more than three hours.

The novel anti-androgenic compositions of the invention are comprised of an anti-androgenically effective amount of at least one compound of Formula I or its non-toxic, pharmaceutically acceptable acid addition salts and an inert pharmaceutical carrier. The compositions may be in the form of tablets, dragees, capsules, syrups, suppositories, creams, pomades, lotions, or injectable solutions prepared in the usual manner.

Examples of suitable excipients are aqueous or non-aqueous vehicles, gum arabic, lactose, starch, magnesium stearate, cocoa butter, fatty bodies of animal of vegetable origin, paraffinic derivatives, glycols, wetting agents, dispersants, emulsifiers, and preservatives.

The compositions inhibit the effect of androgens on peripherical receptors and have an anti-androgenic activity useful for therapy in adults without the certain effects of a chemical castration. The compositions are useful for the treatment of adenoma and neoplasia of the prostate as well as benign hypertrophia of the prostrate, they are also useful for the treatment of benign or malignant tumors of cells containing androgen receptors. They are particularly useful for the treatment of breast, brain, skin and ovarian cancer and bladder, lymphatic system, liver, and kidney cancers. They are equally useful for the treatment of hirsutism, acne, seborrhea, androgenic alopecia, hyperpilosity, and in the veterinary field.

The compositions of the invention are useful in dermatology and can contain another ingredient such as an antibiotic, e.g. derivatives of azelaic acid, fusidic acid, erythromycin or with a derivative of retinoids for the treatment of acne. They can also be used with a 5α-reductase inhibitor such as (5α, 17β)-1,1-dimethylethyl 3-oxo 4-aza$\Delta^1$-androstene-17 carboxamide (or Finasteride Merck, 11th ed.) or with azelaic acid or a blocking agent of androgen receptors for the treatment of acne, alopecia or hirsutism. In addition, they can be used with a product stimulating the growth of hair such as Minoxidil for the treatment of alopecia. The compositions can also be used in the veterinary domain and in the form of radioactive products, as well as in diagnostics as specific labels for the androgen receptors. As radioactive products they can be labeled with tritium, carbon 14, and/or iodine 125.

The novel method of the invention for inducing anti-androgenic activity in warm-blooded animals, including humans, comprises administering to the warm-blooded animals an anti-androgenically effective amount of at least one compound of Formula I and its non-toxic, pharmaceutically acceptable acid addition salts. The compounds may be administered parenterally, buccally, perlingually, rectally, or topically and the usual daily dose is 0.13 to 6.66 mg/kg depends on the condition treated, the specific compound, and the method of administration.

The starting compounds of Formula II may be prepared by reacting phosgene, when X is oxygen, or thiophosgene, when X is sulfur, with an amine of the formula

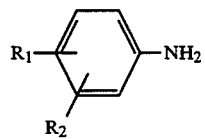

A

A product of this type is described in French Patent No. 2,329,276. The amines of formula A are described in EP Patent No. 0,002,892 and French Patent No. 2,142,804.

The products of Formula III or III' are known or can be prepared from the corresponding cyanhydrins by the process described in J. Am. Chem. Soc., Vol. 75 (1953), p. 4841, or Beil. I, 4 526, or J. Org. Chem., Vol. 27 (1962), p. 2901. The compounds of Formula III wherein R'$_3$ is other than hydrogen may be obtained by reacting a compound of the formula R''$_3$ Hal with 2-cyano-2-aminopropane under the conditions described above for reacting the said halide with the compounds of Formula IV. An example is described by Jilek et al, Collect. Czech. Chem. Comm., Vol. 54(8) 1989), p. 2248. The products of Formula IV' are described in French Patent No. 2,329,276.

The compounds of formulae V and VI are commercially available known compounds and can be prepared by known methods.

The preparation of the compounds of Formula VI are described in the following publications: Zhur Preklad Khim., Vol. 28 (1955), p. 969–75 (CA, Vol. 50 (1956), p. 4881 a); Tetrahedron, Vol. 43 (1987), p. 1753; J. Org. Chem., Vol. 52 (1987), p. 2407; Zh. Org. Khim., Vol. 21 (1985), p.2006; J. Fluor. Chem., Vol. 17 (1981), p. 345; German Patent 637,318, European Patent 0,130,875, and Japanese Patent No. 81-121,524.

The products of Formula VI which are derivatives of hydantoin are largely used and are known in the literature such as J. Pharm. Pharmacal., 67, Vol. 19(4) (1967), p. 209–16; J. Chem. Soc., Vol. 74(2) (1972), p. 219–221; Khim. Farm. Zh., Vol 67(1)(5), p. 51–2; German Patent 2,217,914; European Patent 0,091,596 and J. Chem. Soc. Perkin. Trans. 1, Vol. 74(2), p. 48 and 219–221.

The novel intermediates of the invention are the compounds of the formula

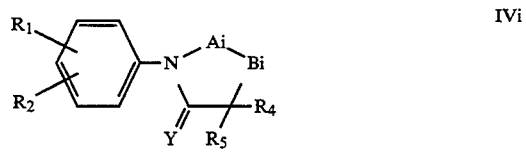

IVi wherein R$_1$, R2 and Y have the above definitions and -Ai-Bi- is

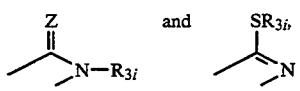

wherein X is oxygen or sulfur and R$_{3i}$ is R$_3$ with the reactive groups, among which are —OH and —NH$_2$, protected as above for R$_3$.

In the following examples, there are described several preferred embodiments to illustrate the invention. However, it should be understood that the invention is not intended to be limited to the specific embodiments.

EXAMPLES

Example 1

4-(3-methyl-5-oxo-2-thioxo-1-imidazolidinyl)-2-trifluoromethyl-benzonitrile a. A solution of 22 ml of distilled water and 1 ml of thilphosgene were slowly added to 2.23 g of 2-trifluoromethyl-4-amino-benzonitrile (prepared as in EP 000 2892) and the mixture was stirred for 1 hour and then extracted chloroform. The organic phase was washed with aqueous sodium chloride, dried, and evaporated to dryness under reduced pressure to obtain 3 grams of the desired product which was used as is.

b. A solution of 976 mg of N-methylglycyne in 3.65 ml of 3 mol sodium hydroxide solution was added to 2.5 grams of the thioisocyanate of Step a) in solution in 5 ml of ethanol. The mixture was stirred for 30 minutes at room temperature and then refluxed for 1 hour. After returning to room temperature, the mixture was poured into a mixture of 20 ml of water and 10 ml of N-hydrochloric acid and extracted with chloroform. After chromatography over silica (elution with methylene chloride-acetone (95–5)), there was obtain 1.78 grams of product which was crystallized from a mixture of methylene chloride and cyclohexane to obtain 1.66 g of the desired product melting at 220° to 221° C. and having an Rf=0.18 (cyclohexane-ethyl acetate 1—1).

IR Spectrum CHCl$_3$:

| | |
|---|---|
| C=O | 1788–1729 cm$^{-1}$ |
| C≡N | 2235 cm$^{-1}$ |
| conjugated system + Aromatics | 1614–1580–1515 cm$^{-1}$ |

UV Spectrum (EtOH):

| | | |
|---|---|---|
| Max. | 232 nm | $\epsilon$ = 17,300 |
| Max. | 254 nm | $\epsilon$ = 22,700 |

Example 2

4-[1-methyl-4-imino-2-thioxo-1,3-diazaspiro(4,4)nonan-3-yl]-2-trifluoromethyl-benzonitrile A solution of 1.36 g of 1-methylamino-cyclopentane carbonitrile in 10 ml of tetrahydrofuran were added over about 2 minutes to 2.5 g of the isocyanate of step a of Example 1 and the mixture was stirred for 40 minutes. The solvent was evaporated and the residue was chromatographed over silica (elution with methylene chloride-ethyl acetate (87.5–12.5)) to obtain 3.32 g of the expected product melting at 165°–166° C. and having an Rf=0.3 (methylene chloride-ethyl-acetate (85–15)).

IR Spectrum CHCl$_3$:

| | |
|---|---|
| =NH | 3310–1672 cm$^{-1}$ |
| C≡N | 2230 cm$^{-1}$ |
| Aromatics | 1614–1577–1505 cm$^{-1}$ |

Preparation of 1-methylamino-cyclopentane-carbonitrile:

A solution of 6.5 of potassium cyanide in 13 ml of water was added at 15°–20° C. to a solution of 8.5 g of cyclopentanone and 7 g of methylamine hydrochloride in 7.5 ml of water and returned to room temperature; the mixture was stirred for 18 hours and extracted with methylene chloride. The organic phase was washed with aqueous sodium chloride, dried, and evaporated to dryness, and the residue was distilled to obtain 4.1 g of the expected product with a boiling point of 60° C.±0.3° C. at 7 mm of Hg.

Example 3

4-(1-methyl-4-oxo-2-thioxo-1,3-diazaspiro(4,4)nonan-3-yl)-2-trifluoromethyl-benzonitrile 52 ml of methanol were added to a solution of 5.2 ml of chloroform and to 259 mg of the product of Example 2 and then 7.5 ml of 2N-hydrochloric acid were added thereto. The mixture was refluxed for 1 hour and, after cooling to room temperature, was poured into 150 ml of iced water. The mixture was extracted with chloroform and the organic phase was washed aqueous sodium chloride dried and evaporated to dryness. The residue was chromatographed over silica, eluting with ethyl acetate-cyclohexane(3–7) to obtain the fractions with Rf equal to 0.35. After crystallization, from a mixture of methylene chloride and cyclohexane, 247 mg of the desired product, melting at 162° C.–163° C. and with an Rf=0.35 (cyclohexane-ethyl acetate (7–3)) were obtained.

IR Spectrum CHCl$_3$:

| | |
|---|---|
| C=O | 1765 cm$^{-1}$ |
| CN | 2235 cm$^{-1}$ |
| Aromatics | 1609–1578–1505 cm$^{-1}$ |

UV Spectrum (EtOH):

| | | |
|---|---|---|
| Max. | 234 nm | $\epsilon$ = 17,600 |
| Max. | 256 nm | $\epsilon$ = 23,800 |
| Inf. | 266 nm | $\epsilon$ = 20,300 |

Example 4

4-(4,4-diethyl-3-methyl-5-imino-2-thioxo-1-imidazolidinyl)-2-trifluoromethyl-benzonitrile Using the procedure of Example 2, 2.5 g of the isothiocyanate of Step a) of Example 1 and 1.39 g of the appropriate amino nitrile were reacted to obtain 3.22 g of the expected product melting at 167° C.–168 ° C. and having an Rf=0.27 (methylene chloride-ethyl acetate (85–15)) .

IR Spectrum CHCl$_3$:

| | |
|---|---|
| =NH | 1304–1673 cm$^{-1}$ |
| C≡N | 2230 cm$^{-1}$ |
| Aromatics | 1614–1576–1505 cm$^{-1}$ |

Preparation of 1-methyl amino-diethyl-carbonitrile

Using the procedure of Example 2, 8.6 g of diethyl ketone were reacted to obtain 4.8 g of the expected product with a boiling point of 77° C. at 40 mm of Hg.

Example 5

4-(4,4-diethyl-3-methyl-5-oxo-2-thioxo-1imidazolidinyl)-2-trifluoromethyl-benzonitrile Using the procedure of Example 3, 321 mg of the product of Example 4 and 65 ml of methanol and 14 ml of 2 N-hydrochloride acid were reacted to obtain 249 mg of the expected product melting at 126° C.–127° C. and having an Rf=0.45 (cyclohexane-ethyl acetate (4–6)).

IR Spectrum CHCl$_3$:

| | |
|---|---|
| C=O | 1753 cm$^{-1}$ |
| C≡N | 2235 cm$^{-1}$ |
| Aromatics | 1615–1580–1504 cm$^{-1}$ |

UV Spectrum (EtOH):

| | | |
|---|---|---|
| Max. | 234 nm | $\epsilon$ = 17,800 |
| Max, | 254 nm | $\epsilon$ = 24,100 |
| Inf. | 265 nm | |

Example 6

4-(5-methyl-8-imino-6-thioxo(5,7-diazaspiro(3,4))-octan-7-yl-2-trifluoromethyl-benzonitrile A solution of 221 mg of 1-methyl amino-cyclobutanecarbonitrile in 1 mg of 1,2-dichloroethane was added over 3 minutes to a solution of 456 mg of the isothiocyanate of Example 1 Step a) in 2 ml of 1,2-dichloroethane in the presence of 0.2 ml of triethylamine and, after stirring the mixture for 45 minutes, the solution was evaporated. The residue was chromatographed over silica and diluted with a methylene chloride-acetate (95–5) mixture to recover the fraction with an Rf=0.32. After crystallization from ether 610 mg of the expected product melting at 172° C.–173° C. was obtained.

IR Spectrum CHCl3:

| C=NH | 3015–1673 cm⁻¹ |
| C≡N | 2236 cm⁻¹ |
| aromatics | 1615–1580–1505 cm⁻¹ |

Using the procedure of Example 2, 7 g of cyclobutanone were reacted to obtain 10.6 g of 1-methylamino-cyclobutane-carbonitrile.

Example 7

4-(5-methyl-8-oxo-6-thioxo(5,7-diazaspiro(3,4))-octan-7-yl)-2-trifluoromethyl-benzonitrile Using the procedure of Example 3, 514 mg of the product of Example 6 and 1.5 ml of 2N-hydrochloric acid were reacted to obtain, after chromatography over silica (cyclohexane-ethyl acetate (6–4)) to obtain a fraction with an Rf=0.34. Crystallization from ether yielded 499 mg of the expected product melting at 161° C.–162° C.

IR Spectrum CHCl3:

| C=O | 1754 cm⁻¹ |
| C≡N | 2236 cm⁻¹ |
| aromatics | 1615–1583–1504 cm⁻¹ |

UV Spectrum (EtOH):

| Inf. | 239 nm | ε = 17,400 |
| | 257 nm | ε = 21,200 |
| | 268 nm | ε = 19,000 |

Example 8

4-(1-methyl-4-imino-2-oxo-1,3-diazaspiro (4,4))-nonan-3-yl)-2-trifluoromethyl-benzonitrile 1.5 ml of a solution of the isocyanate of 3-trifluoromethyl-4-benzonitrile of Example 1 starting from phosgene and 2-trifluoromethyl-4-benzonitrile (1.6M/l) in 1,2 dichloroethane were added at −3° C. to a solution 300 mg of 1-methylamino-cyclopentanecarbonitrile in 3 ml of 1,2 dichloroethane in the presence of 0.5 ml of triethylamine; after stirring for 40 minutes, the solution was evaporated to dryness. The residue was chromatographed over silica and diluted with a methylene chloride-ethyl acetate (95–5) mixture to obtain 620 mg of the expected product.

Example 9

4-(1-methyl-2,4-dioxo-1,3-diazaspiro(4,4))-nonan-3-yl)-2-trifluoromethyl-benzonitrile A mixture of 535 mg of the product of Example 8 in 10 ml of methanol and 2 ml of 2N-hydrochloric acid was heated at 50° C. with stirring for 1 hour and, after returning to the room temperature, 20 ml of water were added thereto. The mixture was extracted with methylene chloride and the organic phase was evaporated to dryness under the reduced pressure. The residue was dissolved in acetone and chromatographed over silica (methylene chloride-acetone (98–2)) to obtain 325 mg of the expected product.

IR Spectrum CHCl3:

| C=O | 1777(m), 1724 cm⁻¹(F) |
| C≡N | 2238 cm⁻¹ |
| Aromatics | 1616–1576–1505 cm⁻¹ |

UV Spectrum (EtOH):

| Inf. | 236 nm | ε = 10,000 |
| Max. | 262 nm | ε = 13,900 |
| Inf. | 277 nm | ε = 7,200 |
| Inf. | 286 nm | ε = 3,700 |

Example 10

4-(5-methyl-8-imino-6-oxo-5,7-diazaspiro(3,4))-octan-7-yl)-2-trifluoromethyl-benzonitrile Using the procedure of Example 8, 2 ml of a solution of isocyanate and 352 mg of 1-methylamino-cyclobutane-carbonitrile were reacted to obtain, after chromatography over silica (eluant methylene-chloride ethyl acetate (85–15)), the product with Rf=0.20 and finally to obtain 301 mg of the expected product melting at 144° C.–145° C.

IR Spectrum CHCl3:

| OH/NH | 3295 cm⁻¹ |
| C≡N | 2240 cm⁻¹ |
| C=O | 1740 cm⁻¹ |
| C=N | 1664 cm⁻¹ |
| aromatics | 1611–1572–1508 cm⁻¹ |

Example 11

4-(6,8-dioxo-5-methyl-5,7-diazaspiro(3,4))-octan-7-yl)-2-trifluoromethyl-benzonitrile Using the procedure of Example 9, 0.8 g of the product of Example 10 and 3 ml of 2N-hydrochloric acid were reacted and chloroform was used as the extraction solvent. After chromatography over silica (methylene chloride-ethyl acetate (95–5)), there were obtained 465 mg of the expected product melting at 165° C.–166° C.

IR Spectrum CHCl3:

| C≡N | 2236 cm⁻¹ |
| C=O | 1778, 1726 cm⁻¹ |
| Aromatics | 1616–1579–1505 cm¹ |

UV Spectrum (EtOH):

| Max. | 238 nm | ε = 11,000 |
| Max. | 262 nm | ε = 14,000 |
| Inf. | 278–286 nm | |

Example 12

4-(4-imino-2-oxo-1,3-diazaspiro(4,4))-nonan-3-yl)-2-trifluoromethyl-benzonitrile Using the procedure of Example 8, 3.1 ml of 1.6M solution of isocyanate and 550 mg of 1-imino-cyclopentane-carbonitrile were reacted to obtain, after chromatography on silica (methylene chloride-acetone (90–10)), 1.24 g of the expected product melting at 212° C.–213° C.

IR Spectrum CHCl3:

| OH/NH | 3350, 3290 cm$^{-1}$ |
|---|---|
| C≡N | 2240 cm$^{-1}$ |
| C=O | 1744 cm$^{-1}$ |
| C=N | 1678 cm$^{-1}$ |
| Aromatics | 1610–1574–1510 cm$^{-1}$ |

Preparation of 1-amino-cyclopentane-carbonitrile 8.8 ml of cyclopentane were added dropwise at 0° to 8° C. to a mixture of 7.9 g of ammonium chloride, 6.14 g of sodium cyanide and 40 ml of ammonium hydroxide and, after returning to room temperature, the mixture was stirred for 16 hours and extracted with methylene chloride. The organic phase was washed with aqueous sodium chloride, dried, and evaporated to dryness at a temperature less than 30° C. The residue was distilled to obtain 11 g of the expected product with a boiling point of 55° C.±2° at 11 mg of Hg.

Example 13

4-(2,4-thioxo-1,3-diazaspiro(4,4))-nonan-3-yl)-2-trifluoromethyl-benzonitrile

Using the procedure of Example 9, 1.17 g of the product of Example 12 and 5 ml of 2 N-hydrochloric acid were reacted to obtain, after chromatography on silica (methylene chloride-acetone (9-1)), 1.108 g of the expected product with a melting point of 184° C.–185° C. and having an Rf=0.23.

IR Spectrum CHCl$_3$:

| =C—NH | 3444 cm$^{-1}$ |
|---|---|
| C≡N | 2296 cm$^{-1}$ |
| C=O | 1786, 1731 cm$^{-1}$ |
| Aromatics | 1616–1505 cm$^{-1}$ |

UV Spectrum (EtOH):

| Max. | 258 nm | $\epsilon$ = 15,600 |
|---|---|---|
| Max. | 286 nm | $\epsilon$ = 3,500 |

Example 14

4-(8-imino-6-oxo-5,7-diazaspiro(3,4))-octan-7-yl)-2-trifluoromethyl-benzonitrile Using the procedure of Example 8, 3.1 ml of an isocyanate solution and 480 mg of 1-amino-cyclobutane-carbonitrile were reacted to obtain 990 mg of the expected product melting at 192° C.–193° C. and having an Rf=0.25.

IR Spectrum CHCl$_3$:

| OH/NH | 3380, 3315 cm$^{-1}$ |
|---|---|
| C≡N | 2240 cm$^{-1}$ |
| C=N | 1754 cm$^{-1}$ |
| Aromatics | 1612–1571–1510 cm$^{-1}$ |

Using the procedure of Example 12, 7.4 ml of cyclobutanone were reacted to obtain 9.2 g of 1-amino-cyclobutane-carbonitrile.

Example 15

4-(6,8-dioxo-5,7-diazaspiro(3,4))-octan-7-yl)-2-trifluoromethyl-benzonitrile

Using the procedure of Example 9, a solution of 327 ml of the product of Example 14 in 1.5 ml of chloroform and 1.9 ml of 2N-hydrochloric acid were reacted to obtain, after chromatography on silica (methylene chloride-acetone (9-1)), 341 mg of the expected product melting at 210° C.–211° C. and having an Rf=0.32.

IR Spectrum CHCl$_3$:

| OH/NH | 3390 cm$^{-1}$ |
|---|---|
| C≡N | 2240 cm$^{-1}$ |
| C=N | 1787, 1737 cm$^{-1}$ |
| Aromatics | 1612–1577–1508 cm$^{-1}$ |

UV Spectrum (EtOH):

| Max. | 259 nm | $\epsilon$ = 15,700 |
|---|---|---|
| Inf. | 277, 286, 301 nm | |

Example 16

4-[1-(4-hydroxybutyl(2,4-dioxo-1,3-diazaspiro(4,4))-nonan-3-yl]-2-trifluoromethyl-benzonitrile A solution of 808 mg of the product of Example 13, in 7 ml of dimethylformamide were added dropwise over 35 minutes to 142 mg of sodium hydride and, 10 minutes after the evolution of hydrogen disengagement, 650 mg of 4-chloro-tert.-butyldimethylsilyl ether and 408 mg of sodium iodide were added. The mixture was heated at 70° C. for 3 hours and, after returning to room temperature, 71 mg of sodium hydride were added. The mixture was stirred for 10 minutes and 330 mg of the silyl were reacted and 222 mg of sodium iodide were added thereto. The mixture was heated for 45 minutes at 70° C. and, after cooling to room temperature, 60 ml of water containing about 500 mg of monopotassium phosphate were added thereto. The mixture was extracted with ethyl ether and then with ethyl acetate and the combined organic phases were dried and evaporated to dryness under reduced pressure. The residue was chromatographed over silica (methylene chloride-acetone (98-2)) to obtain 560 mg of the silyl intermediate. 550 mg of the silylated intermediate were added to 6 mg of methanol and 1.5 ml of 2N hydrochloric acid, and the mixture was stirred for 30 minutes. 30 ml of water was added and the mixture was extracted with methylene chloride. The organic phase was dried and evaporated to dryness and the residue was chromatographed over silica (methylene chloride-acetone (9-1)) and then crystallized from isopropylether to obtain 381 mg of the expected product melting at 125°–126° C. and having an Rf=0.17.

IR Spectrum CHCl$_3$:

| OH | 3625 cm$^{-1}$ |
|---|---|
| C≡N | 2235 cm$^{-1}$ |
| C=N | 1773, 1721 cm$^{-1}$ |
| Aromatics | 1615–1580–1505 cm$^{-1}$ |

UV Spectrum (EtOH):

| Max. | 239 nm | $\epsilon$ = 9,800 |
|---|---|---|
| Max. | 262 nm | $\epsilon$ = 14,600 |
| Inf. | 286 nm | |

Example 17

4-[5-(4-hydroxybutyl(-6,8-dioxo-5,7-diazaspiro(3,4))-octan-7-yl]-2-trifluoromethyl-benzonitrile Using the procedure of Example 16, the product of Example 15 was reacted to obtain the expected product melting at 92° C.–93° C.
IR Spectrum CHCl3:

| OH | 3626 cm$^{-1}$ |
| C≡N | 2235 cm$^{-1}$ |
| C=O | 1775(m), 1784 cm$^{-1}$(F) |
| aromatics | 1616–1578–1505 cm$^{-1}$ |

UV Spectrum (EtOH):

| Max. | 238 nm | ε = 11,200 |
| Max. | 262 nm | ε = 13,900 |
| Inf. | 288 nm | |

Using the procedure of the above Examples, the appropriate isocyanate or thioisocyanate and 3,3,3-trifluoromethyl- 2-trifluoromethyl-2-methylamino-propionitrile prepared according to J. Org. Chem., Vol. 35, p. 1485 (1970) were reacted to obtain the following compounds.

Example 18
4-(4,4-bis,trifluoromethyl-3-methyl-5-imino-2-thioxo-1-imidazolidinyl)-2-trifluoromethyl-benzonitrile

Example 19
4-(4,4-bis,trifluoromethyl-3-methyl-5-oxo-2-thioxo-1-imidazolidinyl)-2-trifluoromethyl-benzonitrile

Example 20
4-(4,4-bis,trifluoromethyl-3-methyl-5-imino-2-oxo-1-imidazolidinyl)-2-trifluoromethyl-benzonitrile

Example 21
4-(4,4-bis,trifluoromethyl-3-methyl-2,5-dioxo-2-thioxo-1-imidazolidinyl)-2-trifluoromethyl-benzonitrile

Example 22

Tablets were prepared by combining 100 ml of the product of Example 3, with sufficient excipient comprising lactose amido talc and magnesium stearate to form a final tablet weight of 300 mg.

In addition to the above products, other compounds falling within the scope of the invention are those having the following formula wherein $R_1$, $R_2$, $R_3$ $R_4$, $R_5$ and X are as indicated in the following table.

| $R_1$ | $R_2$ | X | Y | $R_4$ | $R_5$ |
|---|---|---|---|---|---|
| C≡N | CF$_3$ | S | O | | ◁▷ |
| " | " | O | " | | " |
| " | " | S | " | | ⬡ |
| " | " | O | " | | " |

PHARMACOLOGICAL DATA

1) Study of androgenic Receptors

Male rats of the Sprague Dawley EOPS strain weighing 180 to 200 g, castrated 24 hours previously, were killed and the prostate was removed, weighed and homogenized at 0° C. with a potter glass in a buffered solution (Tris 10 mM, saccharose 0.25M, PMSF (phenyl methane sulfonyl fluoride) 0.1 mM, sodium molybdate 20 mM, HCl pH 7.4 into which was added extemporaneously 2 m of DTT (DL dithiothreitol) at a rate of 1 g of tissue per 8 ml of buffer solution. The homogenate was then ultracentrifuged at 0° C. for 30 minutes at 209,000 g and the aliquots of supernatant (=cytosol) were incubated for 30 minutes and 24 hours with a concentration (T) of tritiated testosterone and in the presence of increasing concentrations (0 to 2500×10$^{-9}$M) of cold testosterone or the test products. The concentration of bound tritiated testosterone (B) was then measured for each incubate by adsorption method of carbondextran. The relative affinity of bonding (RBA) was calculated.

The following two curves were graphed: the percentage of the bound tritiated hormone B/T as a logarithmic function of the concentration of the cold hormone and B/T as a logarithmic function of the concentration of the tested cold product. The line of the equation $$I_{50} = \frac{(B/T\text{max} + B/T\text{min})}{2}$$

was determined.

B/T max=% of the bound tritiated hormone for an incubation of this tritiated hormone at concentration (T).

B/T min=% of the bound tritiated hormone for an incubation of this tritiated hormone at the concentration (T) in the presence of a large excess of cold hormone (2,500×10$^{-9}$M).

The intersection of the straight line I$_{50}$ and the curves permit an evaluation of the concentrations of the cold reference hormones (CH) and the cold test product (CX) which inhibit by 50% the bonding of the tritiated hormone on the receptor. The RBA of the test product was determined by the equation

RBA=100(CH)/(CX)

and the following results expressed in RBA were obtained with testosterone=100.

| Products of example | Incubation 24 H |
|---|---|
| 3 | 27 |

-continued

| Products of example | Incubation 24 H |
|---|---|
| 5 | 8 |

2) Determination of the androgen or anti-androgen activity by the dosage of ornithine carboxylase Six week old male Swiss mice castrated 24 hours received oral dose of the test products as a 0.5% suspension in methyl cellulose or in ethanol by oral or percutaneous route simultaneously with a sub-cutaneous injection of 3 mg/kg of testosterone propionate in solution in corn oil to determine the anti-androgen activity. Active agonists were determined in the absence of testosterone propionate. The test compounds as well as testosterone were administered in a volume of 10 ml/kg. 20 hours after the treatments, the animals were killed, the kidneys were removed and then homogenized at 0° C. with a teflon-glass grinding apparatus in 10 volumes of buffer Tris-HCl 50 mM at a pH 7.4 containing 250 µM of pyridoxal phosphate, 0.1 mM EDTA and 5 mM of dithiothreitol. The homogenate was centrifuged at 209,000 g for 30 minutes.

At 37° C., renal ornithine decarboxylase transforms an isotopic mixture of cold ornithine and tritiated ornithine in cold putrescine and tritiated putrescine. The putrescine was then collected on selective ion-exchange papers, after drying, excess non-transformed cold and tritiated ornithine were eliminated by washing 3 times with 0.1M ammonium hydroxide. The papers were dried and the radioactivity was determined after addition of an Aqualite sample. The results expressed in fmoles ($10^{-15}$M) of tritiated putrescine formed per hour/mg of protein are reported in the following table.

| Products of Example | % Inhibition of ODL Test A |
|---|---|
| 3 | 28 |
| 5 | 43 |

CONCLUSION

The tests show that the tested compounds of the invention possess a strong anti-androgen activity and are devoid of agonist activity.

Various modifications of the compounds and method of the invention may be made without departing from the spirit or scope thereof and it is to be understood that the invention is intended to be limited only as defined in the appended claims.

What is claimed is:

1. A method of inducing anti-androgenic activity in warm-blooded animals comprising administering to warm-blooded animals an anti-androgenically effective amount of at least one compound selected from the group consisting of compounds of the formula

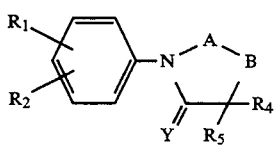

I wherein $R_1$ and $R_2$ are individually selected from the group consisting of —CN, —NO$_2$, halogen, —CF$_3$, free carboxy, salified carboxy and carboxy esterified with lower alkyl; -A-B- is selected from the group consisting of

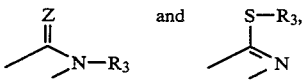

wherein X is =O or =S, $R_3$ is selected from the group consisting of hydrogen, alkyl, alkenyl, alkynyl, carbocyclic aryl and carbocyclic aralkyl each of up to 12 carbon atoms, all optionally substituted with at least one member of the group consisting of —OH, halogen, —SH, —CN, acyl of up to 7 carbon atoms acyloxy of up to 7 carbon atoms, —S— carbocyclic aryl of up to 12 carbon atoms optionally substituted with a member of the group consisting of —CF$_3$, alkyl, alkoxy, alkenyl, alkenyloxy, alkynyl, and alkynyloxy, with the sulfur being optionally oxidized to sulfone or sulfoxide, free, esterified, amidified or salified carboxy, —NH$_2$, mono and dialkylamino, and when the latter alkyl, alkenyl and alkynyl being optionally interrupted with at least one member of the group consisting of oxygen, nitrogen, and sulfur said sulfur being optionally oxidized to sulfoxide or sulfone, Y is =O, =S, or =NH; $R_4$ and $R_5$ taken together with the carbon atom to which they are attached, form cycloalkyl of 3 to 7 carbon atoms and their non-toxic, pharmaceutically acceptable acid addition salts.

2. A method of claim 1 wherein Y is —O—, -A-B- is

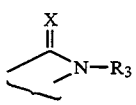

and X and $R_3$ are as defined in claim 1.

3. A method of claim 1 wherein -A-B- is

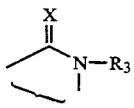

X is as defined is claim 1 and $R_3$ is selected from the group consisting of hydrogen and alkyl of 1 to 6 carbon atoms optionally interrupted with at least one —O— or —S— and optionally substituted with at least one member of the group consisting of —OH, OH esterified with an acyl of an organic carboxylic acid of 1 to 7 carbon atoms, and free, esterified or salified carboxy.

4. A method of claim 1 wherein $R_3$ is hydrogen or alkyl of 1 to 6 carbon atoms optionally substituted by —OH.

5. A method of claim 1 wherein $R_3$ is alkyl of 1 to 4 carbon atoms optionally substituted by —OH.

6. A method of claim 1 wherein $R_2$ is 3—CF$_3$ and $R_1$ is 4—CN.

7. A method of claim 1 wherein $R_4$ and $R_5$ taken together with the carbon atom to which they are attached, form cyclopentyl or cyclobutyl.

8. A method of claim 1 which is 4-[1-methyl-4-oxo-2-thioxo-1,3-diazaspiro-( 4,4 )-nonan-3-yl]-2-trifluoromethylbenzonitrile.

* * * * *